(12) United States Patent
Huynh et al.

(10) Patent No.: US 11,564,967 B1
(45) Date of Patent: *Jan. 31, 2023

(54) ORAL COMPOSITIONS CONTAINING EXTRACTS OF A BETEL LEAF AND RELATED METHODS

(71) Applicant: Nam Linh Huynh, Escondido, CA (US)

(72) Inventors: Tran Ky Huynh, Ho Chi Minh (VN); Nam Linh Huynh, Escondido, CA (US)

(73) Assignee: Tran Ky Huynh, Ho Chi Minh City (VN)

( * ) Notice: Subject to any disclaimer, the term of this patent is extended or adjusted under 35 U.S.C. 154(b) by 0 days.

This patent is subject to a terminal disclaimer.

(21) Appl. No.: 17/648,682

(22) Filed: Jan. 24, 2022

(51) Int. Cl.

| | | |
|---|---|---|
| A61K 36/67 | (2006.01) |
| A61K 36/00 | (2006.01) |
| A61K 36/54 | (2006.01) |
| A61K 36/752 | (2006.01) |
| A61K 35/644 | (2015.01) |
| A61K 31/05 | (2006.01) |
| A61K 36/484 | (2006.01) |
| A61K 36/82 | (2006.01) |
| A61K 36/53 | (2006.01) |
| A61K 36/9066 | (2006.01) |
| A61K 36/61 | (2006.01) |
| A61K 36/886 | (2006.01) |
| A61K 36/68 | (2006.01) |
| A61K 36/899 | (2006.01) |
| A61K 36/889 | (2006.01) |
| A61K 47/42 | (2017.01) |
| A61K 9/00 | (2006.01) |
| A61P 31/14 | (2006.01) |
| A61K 36/9068 | (2006.01) |

(52) U.S. Cl.
CPC ............ *A61K 36/67* (2013.01); *A61K 9/0053* (2013.01); *A61K 31/05* (2013.01); *A61K 35/644* (2013.01); *A61K 36/484* (2013.01); *A61K 36/53* (2013.01); *A61K 36/54* (2013.01); *A61K 36/61* (2013.01); *A61K 36/68* (2013.01); *A61K 36/752* (2013.01); *A61K 36/82* (2013.01); *A61K 36/886* (2013.01); *A61K 36/889* (2013.01); *A61K 36/899* (2013.01); *A61K 36/9066* (2013.01); *A61K 36/9068* (2013.01); *A61K 47/42* (2013.01); *A61P 31/14* (2018.01); *A61K 2236/331* (2013.01); *A61K 2236/333* (2013.01)

(58) Field of Classification Search
None
See application file for complete search history.

(56) References Cited

U.S. PATENT DOCUMENTS

| | | | | |
|---|---|---|---|---|
| 6,623,767 B1 * | 9/2003 | Morice | ............... | A61K 8/922 |
| | | | | 424/47 |
| 2004/0247669 A1 * | 12/2004 | Gin | ............ | A23L 27/72 |
| | | | | 424/468 |
| 2007/0218555 A1 * | 9/2007 | Paknikar | ............ | A61K 9/10 |
| | | | | 435/317.1 |
| 2012/0244087 A1 * | 9/2012 | Trivedi | ............ | A61K 8/9794 |
| | | | | 424/48 |
| 2021/0022967 A1 * | 1/2021 | Tao | ............ | A61K 8/44 |

FOREIGN PATENT DOCUMENTS

| | | | |
|---|---|---|---|
| CN | 111484909 A | * | 8/2020 |
| VN | 40058 A | * | 11/2014 |
| WO | WO9216182 A2 | * | 10/1992 |

\* cited by examiner

*Primary Examiner* — Michael Barker
*Assistant Examiner* — Randall O Winston (57) ABSTRACT

A *betel* leaf extracts composition having bactericidal, antiviral, and neutralization of virus SARS-CoV-2 properties by oral. The bactericidal, antiviral, and SARS-CoV-2 virus-neutralizing efficacy of *betel* leaf extract/essential oil was increased by the combination with the one or two or more active plant extracts/essential oils ingredients, 4-allylpyrocatechol (APC) ingredient, a mixture of ginger-honey, and a mixture of lemon-kumquat-cinnamon by predefined order and predetermined percentage by weight of each ingredient into an oral cavity delivery agent including a range of gum, confectionery/candy, lozenge, tablet, edible film, oral film, oral solution and oral spray solution.

19 Claims, 2 Drawing Sheets

ORAL COMPOSITIONS CONTAINING EXTRACTS OF A BETEL LEAF AND RELATED METHODS

FIELD OF THE INVENTION

The invention relates to the field of bactericidal and antiviral products. In particular, the present invention relates to the SARS-CoV-2 virus neutralizer agent, which is prepared from plant extracts/essential oils combined with *betel* leaf extract/essential oil, 4-allylpyrocatechol (APC) ingredient, a mixture of ginger-honey, and a mixture of lemon-kumquat-cinnamon. More specifically, the present invention relates to oral compositions containing extracts of a *betel* leaf and related methods.

BACKGROUND ART

COVID-19 is a disease characterized by acute respiratory infections caused by the SARS-CoV-2 virus. Patients infected with the SARS-CoV-2 virus have a wide range of symptoms, ranging from asymptomatic to multi-organ failure. Symptoms are similar to those of other respiratory infections such as fever, dry cough, shortness of breath, muscle aches, confusion, headache, sore throat, chest tightness, diarrhea, and nausea. Severe disease can lead to pneumonia, respiratory failure, and even death in a few patients in the first week after infection because of the dramatic increase in the number of inflammatory cytokines. In addition, underlying medical conditions such as diabetes, hypertension, cardiovascular and respiratory diseases also aggravate the condition.

Until now, the COVID-19 pandemic is still posing a serious threat to humanity, the global economy and society. With its rapidly infective properties, it becomes really difficult to prevent the virus from reaching many populations. In addition to efforts to develop diagnostic reagents, vaccines, and antiviral drugs to protect human lives and slow the spread of the COVID-19 pandemic. The world still needs more traditional methods to fight the SARS-CoV-2 virus.

Since ancient times, in traditional medicine around the world, many herbs have been used to treat respiratory infections such as cough, asthma, colds, bronchitis, flu, respiratory tract infections. Specifically, some species of herbs commonly used to treat respiratory diseases include *betel* nut, ginger, cinnamon, lemongrass, *citrus* trees (of the genus *Citrus*), etc. proven to contain biologically active compounds (Alkaloids, Polyphenols, Flavonoids, Saponins, . . . ) with antiviral effects. To create more preventive measures against the COVID-19 pandemic, the creation of safe and effective products from natural herbal sources with antiviral activity are considered potential products for the prevention and treatment of diseases caused by the SARS-CoV-2 virus.

According to research documents, the *betel* leaf extract contains about 15 to 40 compounds. Depending on species, or different geographical regions, the *betel* leaf extract/essential oil includes the following 9 groups of substances: monoterpenes (such as terpinene, pinene, limonene, thujene, camphene, etc.), sesquiterpenes (such as cadinene, elemene, caryophyllene, cubebene, etc.), alcohols (linalol, terpineol, cadinol, etc.), aldehydes (such as decanal, etc.), acids (such as palmitic acid, etc.), oxides (such as Eucalyptol, etc.), phenols (such as eugenol, chavibetol, chavicol, etc.), phenolic ethers (such as methyl eugenol) and esters (eugenol acetate, chavibetol acetate, etc.). The main components of *betel* leaf extract/essential oil including phenolic compounds and derivatives (eugenol, chavibetol, eugenol acetate, chavibetol acetate, 4-allylpyrocatechol diacetate, 4-allylpyrocatechol) account for a high proportion of about 25%-60% by weight. Accordingly, research show that the *betel* leaf extract/essential oil have inhibitory activity, killing viruses, bacteria, fungi and protozoa.

Besides, the SARS-CoV-2 virus neutralizer activity agent of the *betel* leaf extract/essential oil was tested at the Pasteur Institute in Ho Chi Minh City. In Ho Chi Minh City. The above results were performed at the Pasteur Institute in Ho Chi Minh City that listed in detail in Tables 1, and Tables 2 below, including: (a) Don't cytotoxic to Vero E6 cells; (b) Titers against virus SARS-CoV-2 used in the neutralization reaction is TCID50/0.1 mL: $10^{5.5}$; and (c) *Betel* leaf extract/essential oil has the ability to neutralize the SARS-CoV-2 virus when exposed/exposed to the virus for 30 minutes. This conclusion is a premise for more complete research and development of bactericidal and antiviral products containing *betel* leaves extracts/essential oils, contributing to effective prevention of virus SARS-CoV-2 during the Covid-19 pandemic.

In addition, according to preliminary statistics, our country has nearly 12,000 species of higher vascular plants belonging to more than 2,256 genera, 305 families (accounting for 4% of the total species, 15% of the total genera, 75% of the total number of plant families in the world). Not only playing the role of a green lung to regulate the climate, but the forest flora also brings great potential for medicinal plant resources in particular along with medicinal resources in general.

According to patent application No. WO2021191664A1, the invention refers to a method for making preparations for the treatment of COVID-19 coronavirus and respiratory system diseases, including ingredients of long pepper powder (*Piper longum*), dried ginger powder (*Zingiber officinale*), wild tamarind juice (Emblica *officinalis*). These ingredients are mixed and dried. Then, add pepper powder (*Piper nigrum*) to form a preparation to treat COVID-19 and respiratory system diseases. The composition is mixed with honey and drunk with warm water.

According to patent application No. PH22019000157U1, the invention refers to a process of producing candy utilizing *betel* leaves (*Piper betel*) comprises the following method: a) preparing of ingredients; b) washing of fresh *betel* (*Piper betel*) leaves in a running water; c) extracting of *betel* (*Piper betel*) leaves juice; d) cooking under moderate heat by stirring constantly until sugar dissolves; e) boiling of the mixture in the pot over medium to high heat unity reaching the hard crack stage between 300-310F; f) removing from heat; g) adding peppermint extract; h) cooling down the mixture; i) molding in a molding cups; and j) packing the candies into a polyethylene bag.

According to patent application No. CN105360550A, the invention refers to a *betel* nut aerated candy comprises biotin from *areca* nut, jelly, sugar, honey, polyol, flavoring agent, natural flavoring agent, and water. *Areca* flavored sponge candy is processed in the following steps: dissolving the ingredients in water, and mixing the ingredients evenly, stirring the mixture, and extruding the mixture.

The above inventions meet the specific purposes and requirements of a technical solution. However, the disclosure of the invention does not address the adjustment of the technical parameters in the process of preparing raw materials (*betel* leaves) before performing the extraction. At the same time, the mixing ingredients, the percentage (%) of each ingredient participating in the mixing and the method of performing the steps are also different.

Therefore, it is necessary to create an oral composition containing extracts of a *betel* leaf multi-purpose, effective, safe, no pollution to the environment, strengthen the body's immune system, more specifically coronavirus prevention and health safety for all ages, especially the elderly and children.

Furthermore, it is necessary to create an oral composition containing extracts of a *betel* leaf that have a green, safe, and healthy antibacterial and disinfection regime during the Covid-19 pandemic; and towards the post-Covid-19 epidemic to meet daily civil antibacterial requirements.

Finally, what is needed to provide a method for manufacturing the oral composition containing extracts of a *betel* leaf that includes simple steps, low cost, make use of available raw materials, easy to collect, non-toxic, and environmentally friendly but still ensure the quality and effectiveness of antibacterial and antiviral products, especially the ability to neutralize SARS-CoV-2 virus.

This invention provides solutions to achieve the above goals.

SUMMARY OF THE INVENTION

Accordingly, an objective of the present invention is to provide an oral composition containing extracts of a *betel* leaf to be used for the development and manufacture of antiseptic products with antibacterial, antiviral. At the same time, also be used to develop products such as a range of gum, confectionery/candy, lozenge, tablet, edible film, oral film, a dissolvable, partially dissolvable, or non-dissolvable film or strip, oral solution, and oral spray solution, and the like.

Another objective of the present invention is to an oral composition containing extracts of a *betel* leaf having an antimicrobial active agent and neutralizing for SARS-CoV-2 including a *betel* leaf extracts/essential oil combined with the one or two or more active plant extracts/essential oils ingredients, 4-allylpyrocatechol (APC) ingredient, a mixture of ginger-honey, and a mixture of lemon-kumquat-cinnamon; preferably at least the *betel* leaf extracts/essential oil combined with a lemongrass extracts/essential oil ingredient, 4-allylpyrocatechol (APC) ingredient, the mixture of ginger-honey, and the mixture of lemon-kumquat-cinnamon; preferably at least the *betel* leaf extracts/essential oil combined with the lemongrass extracts/essential oil ingredient, a mint extracts/essential oil ingredient, 4-allylpyrocatechol (APC) ingredient, the mixture of ginger-honey, and the mixture of lemon-kumquat-cinnamon.

Yet another objective of the present invention is to provide an oral composition containing extracts of a *betel* leaf to be used for manufacturing confectionery/candy including a ginger powder having 0.5%-1.5% by weight; a honey solution having 2.5%-7.5% by weight; a lemon pure juice having 2%-5% by weight; a kumquat pure juice having 2%-5% by weight; a cinnamon ingredient having 0.4%-1% by weight; a lemongrass extracts/essential oil ingredient having 0.5% by weight; a mint extracts/essential oil ingredient having 0.5% by weight; a *betel* leaf extracts/essential oil having 0.5% by weight; a gelatin ingredient having 3%-6% by weight; a sweetener ingredient having 50%-70% by weight; 4-allylpyrocatechol (APC) having 0.12%-0.2% by weight; and the remainder is the water ingredient.

In view of the foregoing, another objective of the present invention is to provide an oral composition containing extracts of a *betel* leaf to be used for manufacturing confectionery/candy including a ginger powder having 1% by weight; a honey solution having 5% by weight; a lemon pure juice having 2.5% by weight; a kumquat pure juice having 2.5% by weight; a cinnamon ingredient having 0.5% by weight; a lemongrass extracts/essential oil ingredient having 0.5% by weight; a mint extracts/essential oil ingredient having 0.5% by weight; a *betel* leaf extracts/essential oil having 0.5% by weight; a gelatin ingredient having 4%-5% by weight; a sweetener ingredient having 60% by weight; 4-allylpyrocatechol (APC) having 0.15%-0.18% by weight; and the remainder is the water ingredient.

Finally, the purpose of the invention is to provide an oral composition containing extracts of a *betel* leaf having oral cavity delivery agent confectionery/candy is obtained by a method comprising the steps of:

(i) preparing materials including the *betel* leaf extracts/essential oil, the plant extracts/essential oils ingredients, 4-allylpyrocatechol (APC) ingredient, the mixture of ginger-honey, and the mixture of lemon-kumquat-cinnamon;

wherein the mixture of ginger-honey is obtained by mixing the ginger ingredient and the honey solution combined with stirring 30-40 rpm in five minutes, then fermentation for 30-180 minutes at a temperature of 25° C.-30° C.;

wherein the mixture of lemon-kumquat-cinnamon is obtained by mixing the lemon pure juice with the cinnamon ingredient combined with stirring 30-40 rpm in five minutes, then adding the kumquat pure juice combined with stirring 30-40 rpm in five minutes and soaking for 10-15 minute;

(ii) mixing the material in step (i) in four stages:

stage 1: mixing the water ingredient with the sweetener ingredient combined with stirring 25-50 rpm in 10-15 minutes at a temperature of 75° C.-85° C.;

then, adding the mixture of ginger-honey, and the mixture of lemon-kumquat-cinnamon combined with stirring 25-50 rpm in 3-10 minutes creating a homogeneous solution;

stage 2: stirring the homogeneous solution with 40-70 rpm in 5 minutes;

determining whether degree Brix of the homogeneous solution is had reaches 75°Bx-85°Bx;

if degree Brix of the homogeneous solution not reach 75°Bx-85°Bx, adding the sweetener ingredient, and repeating said steps of stage 2 until said degree Brix of the homogeneous solution having reach 75°Bx-85°Bx;

stage 3: creating a temporary solution by mixing the gelatin ingredient with the homogeneous solution combined with stirring 30-50 rpm in 5 minutes;

stage 4: creating a foundation solution by mixing the 4-allylpyrocatechol (APC) ingredient, the plant extracts/essential oils ingredients, with the *betel* leaf extracts/essential oil, and the temporary solution combined with stirring 50-80 rpm in 1-2 minutes;

(iii) pouring the foundation solution for shaping, then separating and sorting, making sugar coating and packing.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

According to the embodiment of the present invention, the oral composition containing extracts of a *betel* leaf 100 ("composition 100"). Composition 100 can be in the form of gum, confectionery/candy, edible film and similar texture states as a means of delivering ingredients to the oral cavity for the purpose of providing oral benefits such as freshen breath, which has bactericidal, antiviral, and neutralizing for virus SARS-CoV-2. In the present invention and the specification of the present application, "neutralization of virus" or "neutralizing for virus" refers to removing or significantly reducing the infectivity or the growth capacity of the virus. The virus that can be inactivated/neutralized by the virus inactivating agent of the present invention is not particularly limited, and various viruses can be inactivating targets regardless of the genome type or the presence or absence of an envelope.

According to the embodiment of the present invention, the composition 100 is a combination of the *betel* leaf extracts/essential oils with one or two or more plant extracts/essential oils to effective achieve a synergistic bactericidal, antiviral, and neutralizing for virus SARS-CoV-2.

In an aspect of the present invention, the composition 100 is a confectionery/candy used neutralizing for virus SARS-CoV-2 in the oral cavity by delivering confectionery/candy by oral. Confectionery/candy products for this invention may be hard candies, chewy candies, coated chewy center candies and tabletted candies. In another aspect, composition 100 is chewing gum or any variation including but not limited to bubble gums, pellets, gum balls or sticks.

The composition 100 may also include additional ingredients to freshen breath, or promote oral health, or may contain substances that are bactericidal, antiviral, and neutralizing for virus SARS-CoV-2 is derived from plants combined with extracts/essential oils from *betel* leaves.

According to the preferred embodiment of the present invention, the composition 100 includes: an oral cavity delivery agent, an antimicrobial active agent and neutralizing for virus SARS-CoV-2, and other ingredients. The oral cavity delivery agent including a range of gum, confectionery/candy, lozenge, tablet, edible film, oral film, a dissolvable, partially dissolvable or non-dissolvable film or strip, oral solution and oral spray solution. The antimicrobial active agent and neutralizing for virus SARS-CoV-2 including a *betel* leaf extracts/essential oil combined with the one or two or more active plant extracts/essential oils ingredients, 4-allylpyrocatechol (APC) ingredient, a mixture of ginger-honey, and a mixture of lemon-kumquat-cinnamon.

According to the embodiment of the present invention, the plant extracts/essential oils ingredients selected from the one or more that listed in detail in Tables 3, including chinese liquorice (*Glycyrrhiza uralensis* Fisch.), liquorice (*Glycyrrhiza Glabra* L.), tea (*Camellia sinensis*), holy basil (*Ocimum sanctum*), turmeric (*Curcuma domestica*), clove (*Syzygium aromaticum*), aloe vera (*Aloe vera*), globe artichoke (*Cynara Scolymus* L.), roselle (*Hibiscus sabdariffa*), bitter melon (*Momordica charan*), basil (*Ocimum sanctum* L.), pomegranate (*Punica granatum* L.), chamber bitter (*Phyllanthus urinaria* L.), lemon balm (*Melissa officinalis*), mint (*Mentha haplocalyx* Briq.), horseradish tree (*Moringa oleifera* Lam.), white mulberry (*Morus alba* L.), ginger (*Zingiber officinale* Rosc), cinnamon (*Cinnamomum zeylanicum* Blume), broad-leaved plantain (*Plantago major* L.), areca nut palm (*Areca catechu* L.), apricot (*Prunus armeniaca* L.), lanxangia tsaoko (*Lanxangia tsaoko*), avocado (*Persea americana*), lemongrass (*Cymbopogon citratus, Cymbopogon winterianus J., Cymbopogon flexuosus* Stapf.), siamese ginger (*Alpinia officinarum*), red amaranth (*Amaranthus tricolor*), tufuling (*Smilax glabra* Roxb).

According to the embodiment of the present invention, the antimicrobial active agent and neutralizing for virus SARS-CoV-2 including at least the *betel* leaf extracts/essential oil combined with a lemongrass extracts/essential oil ingredient, 4-allylpyrocatechol (APC) ingredient, the mixture of ginger-honey, and the mixture of lemon-kumquat-cinnamon.

According to the preferred embodiment of the present invention, the antimicrobial active agent and neutralizing for virus SARS-CoV-2 including at least the *betel* leaf extracts/essential oil combined with the lemongrass extracts/essential oil ingredient, a mint extracts/essential oil ingredient, 4-allylpyrocatechol (APC) ingredient, the mixture of ginger-honey, and the mixture of lemon-kumquat-cinnamon.

In an aspect of the present invention, other ingredients including a sweetener ingredient, a gelatin ingredient and a water ingredient. The sweetener ingredient selected from the one or more of the following a refined sugar, a jaggery, a malt, a starch molasses, a lactose, an alcohol sugar, an additional sweeteners; wherein said the additional sweeteners selected from a sugar, a high intensity sweetener, a sugar substitute, or a combination thereof. The term "water" in the embodiment of the present invention may include distilled or sterile water, water for which pathogenic microorganisms or parasites are removed, unless the context clearly indicates.

In an aspect of the present invention, the gelatin ingredients extracted from plants or animals; and treated by soaking with water in the respective ratio of 1:2.

According to the embodiment of the present invention, the composition 100 having a ratio of the antimicrobial active agent and neutralizing for virus SARS-CoV-2 and other ingredients having 1:(5.5-9.5).

According to the preferred embodiment of the present invention, the composition 100 having a ratio of the antimicrobial active agent and neutralizing for virus SARS-CoV-2 and other ingredients having 1:(6-7).

According to the embodiment of the present invention, the composition 100 having a ratio of the total of the *betel* leaf extracts/essential oil and plant extracts/essential oils ingredients with the mixture of ginger-honey, and the mixture of lemon-kumquat-cinnamon having (1-3): 12:11.

According to the preferred embodiment of the present invention, the composition 100 having a ratio of the total of the *betel* leaf extracts/essential oil and plant extracts/essential oils ingredients with the mixture of ginger-honey, and the mixture of lemon-kumquat-cinnamon preferably selected a ratio among the ratios of the following 1:12:11; 2:12:11; and 3:12:11.

According to the embodiment of the present invention, the composition 100 having a ratio of the *betel* leaf extracts/essential oil and plant extracts/essential oils ingredients having 1:(1-3).

According to the preferred embodiment of the present invention, the composition 100 having a ratio of the *betel* leaf extracts/essential oil and plant extracts/essential oils ingredients preferably selected a ratio among the ratios of the following 1:2; and 1:1.

In an aspect of the present invention, the composition 100 having the mixture of ginger-honey is obtained by mixing a ratio of a ginger ingredient and a honey solution having 1:5; wherein the ginger ingredient is selected from a ginger powder, or a ginger juice fresh, or a ginger extracts or a ginger pure juice is extracted and concentrated, or a ginger pure juice is extracted and concentrated at a temperature of 100° C.-110° C.

In an aspect of the present invention, the composition 100 having the mixture of lemon-kumquat-cinnamon is obtained by mixing a ratio of a lemon juice:a kumquat juice:a cinnamon ingredient having 5:5:1. The lemon juice is selected from a lemon pure juice, a lemon juice fresh, and mixtures thereof. The kumquat juice is selected from a kumquat pure juice, a kumquat juice fresh, and mixtures thereof. The cinnamon ingredient is selected from a cinnamon powder, or a cinnamon extracts or a cinnamon pure juice is extracted and concentrated, or a cinnamon pure juice is extracted and concentrated at a temperature of 100° C.-110° C.

According to the preferred embodiment of the present invention, the lemon pure juice, the kumquat pure juice replaced by a pure juice/juice fresh of *citrus*/citrus fruits including but not limited to oranges (*Citrus sinensis*), grapefruits (*Citrus paradist*), pomelo (*Citrus maxima/Citrus grandis*), lemons (*Citrus lemon*), limes (*Citrus aurantifoli*), Mandarin/Clementina/Tangerine (*Citrus reticulata* L), that listed in detail in Tables 4 below.

According to the embodiment of the present invention, the composition 100 having a ratio of the antimicrobial active agent and neutralizing for virus SARS-CoV-2 with a total of the sweetener ingredient and the water ingredient, and the gelatin ingredient having (2-3):(15-20): 1.

According to the preferred embodiment of the present invention, the composition 100 having a ratio of the antimicrobial active agent and neutralizing for virus SARS-CoV-2 with a total of the sweetener ingredient and the water ingredient, and the gelatin ingredient preferably selected a ratio among the ratios of the following 2.5:16.5:1; and 2.6:16.4:1.

In an aspect of the present invention, the *betel* leaf extract/essential oil and 4-allylpyrocatechol (APC) ingredient extracted from fresh old *betel* leaves crushed/chopped/or not chopped, immersed are soaked in liquid water, or solvent, or brine solution, or saturated brine solution, or salt-free water/salt-free solution; wherein the total time from harvesting and preserving fresh old *betel* leaves from the *betel* nut tree must be less than 55 minutes; preferably 30-45 minutes.

According to the embodiment of the present invention, a ratio of the *betel* leaf extracts/essential oil and 4-allylpyrocatechol (APC) ingredient having 3:1.

According to the preferred embodiment of the present invention, a ratio of the *betel* leaf extracts/essential oil and 4-allylpyrocatechol (APC) ingredient preferably having three parts of the *betel* leaf extracts/essential oil obtained from fresh, old *betel* leaves distilled with the saturated brine solution corresponds to one part of 4-allylpyrocatechol (APC) ingredient.

According to the another preferred embodiment of the present invention, a ratio of the *betel* leaf extracts/essential oil and 4-allylpyrocatechol (APC) ingredient preferably having three parts of the *betel* leaf extracts/essential oil obtained from fresh, old *betel* leaves distilled with the salt-free water/salt-free solution corresponds to one part of 4-allylpyrocatechol (APC) ingredient.

According to another embodiment of the present invention, the composition 100 further comprising a group consisting of humectants, abrasives, anticaries agents, anticalculus or tartar control agents, anionic carboxylate polymers, viscosity modifiers, surfactants, flavorants, pigments, and mixtures thereof.

According to the preferred embodiment of the present invention, the composition 100 having oral cavity delivery agent is confectionery/candy, the composition 100 is confectionery/candy includes the ingredients listed in Table 5, including: a ginger powder having a first predetermined percentage (%) by weight; a honey solution having a second predetermined percentage (%) by weight; a lemon pure juice having a third predetermined percentage (%) by weight; a kumquat pure juice having a four predetermined percentage (%) by weight; a cinnamon powder having a fifth predetermined percentage (%) by weight; a lemongrass extracts/essential oil having a sixth predetermined percentage (%) by weight; a mint extracts/essential oil having a seventh predetermined percentage (%) by weight; a *betel* leaf extracts/essential oil having a eighth predetermined percentage (%) by weight; a gelatin ingredient having a ninth predetermined percentage (%) by weight; a sweetener ingredient having a tenth predetermined percentage (%) by weight; 4-allylpyrocatechol (APC) ingredient having a eleventh predetermined percentage (%) by weight; a water ingredient having a twelveth predetermined percentage (%) by weight; wherein the sum of said first predetermined percentage (%) by weight to said twelveth percentage (%) by weight adds up to 100% by weight of the composition 100.

In the embodiment of the present invention, percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%.

According to the embodiment of the present invention, the composition 100 is confectionery/candy including a ginger powder having 0.5%-1.5% by weight; a honey solution having 2.5%-7.5% by weight; a lemon pure juice having 2%-5% by weight; a kumquat pure juice having 2%-5% by weight; a cinnamon ingredient having 0.4%-1% by weight; a lemongrass extracts/essential oil ingredient having 0.5% by weight; a mint extracts/essential oil ingredient having 0.5% by weight; a *betel* leaf extracts/essential oil having 0.5% by weight; a gelatin ingredient having 3%-6% by weight; a sweetener ingredient having 50%-70% by weight; 4-allylpyrocatechol (APC) having 0.12%-0.2% by weight; and the remainder is the water ingredient.

According to the preferred embodiment of the present invention, the composition 100 is confectionery/candy including a ginger powder having 1% by weight; a honey solution having 5% by weight; a lemon pure juice having 2.5% by weight; a kumquat pure juice having 2.5% by weight; a cinnamon ingredient having 0.5% by weight; a lemongrass extracts/essential oil ingredient having 0.5% by weight; a mint extracts/essential oil ingredient having 0.5% by weight; a *betel* leaf extracts/essential oil having 0.5% by weight; a gelatin ingredient having 4%-5% by weight; a sweetener ingredient having 60% by weight; 4-allylpyrocatechol (APC) having 0.15%-0.18% by weight; and the remainder is the water ingredient.

Figure 1:
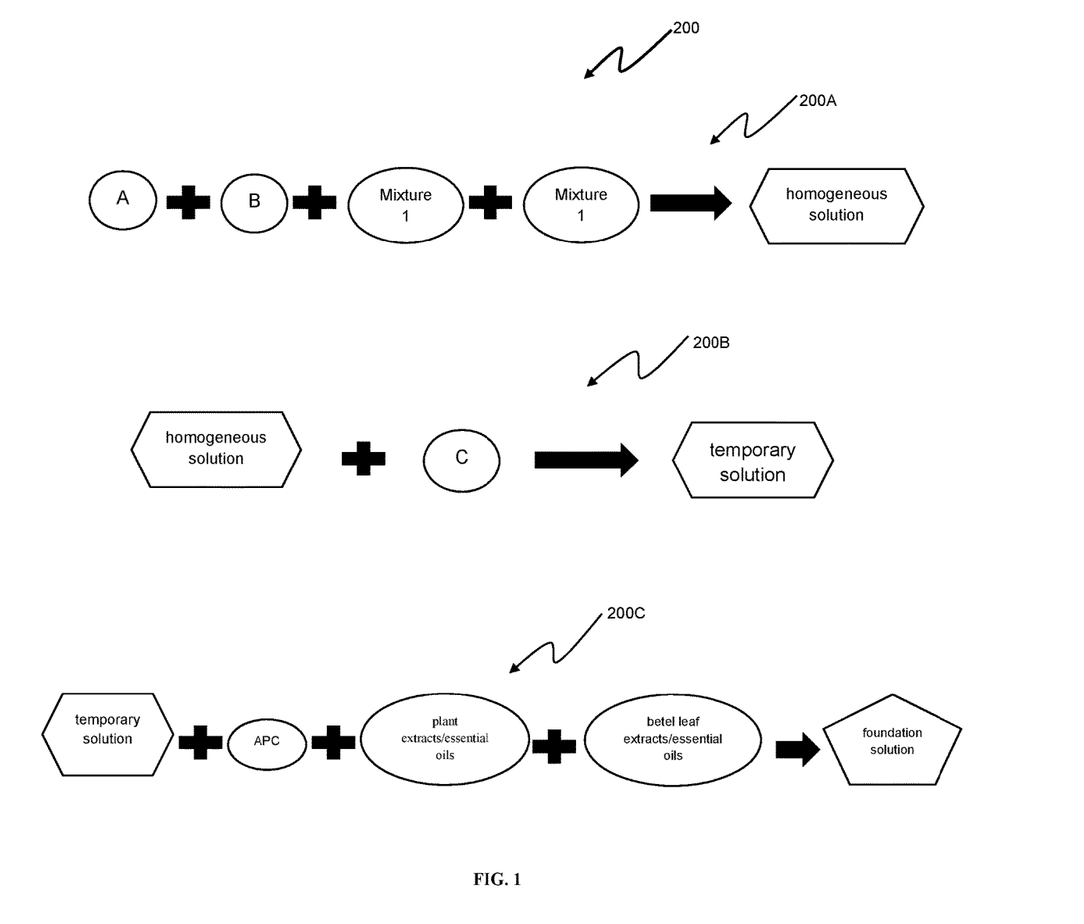
FIG. 1 is a conceptual block diagram illustrating the principle of making the composition having oral cavity delivery agent confectionery/candy in accordance with an exemplary embodiment of the present invention.

One embodiment of the invention is now described with reference to FIG. 1. FIG. 1 illustrates a conceptual block diagram of a method 200 including a first stage 200A, a second stage 200B, and a third stage 200C of manufacturing the composition 100 is confectionery/candy in accordance with an exemplary embodiment of the present invention.

In the first stage 200A, a mixture of at least four ingredients from ingredient A, ingredient B, mixture 1, and mixture 2 is intended to dilute, prolong the time, increasing bactericidal, antiviral, and texturizing activity; to create a homogeneous solution. In many aspects of the present invention, the homogeneous solution is defined as a solution with the following functions: (1) homogeneous dissolution of sweeteners; (2) acting as a reactant, allowing to dissolve extracts/essential oils and other additional compounds of a predetermined percentage (%) by weight; and (3) increasing bactericidal, and antiviral activity. The term "homogeneous" is understood to mean the uniform distribution, or complete dissolution of, substances present in a solution/mixture. According to the embodiment of the present invention, mixture 1 is a mixture of ginger-honey, and mixture 2 is a mixture of lemon-kumquat-cinnamon. Ingredient A is a sweetener ingredient, and ingredient B is a water ingredient, the characteristics of which are mentioned above.

Within the scope of the present invention, the term "homogeneous solution" includes the following meanings: (a) homogeneous solution is a solution that completely dissolves the sweetener ingredient, the water ingredient, the mixture of ginger-honey, and the mixture of lemon-kumquat-cinnamon of a predetermined percentage (%) by weight; (b) homogeneous solution is a solution without the phenomenon of sugar crystallization; (c) homogeneous solution that completely dissolve the plant extracts/essential oils, *betel* leaf extracts/essential oils, 4-allylpyrocatechol (APC) ingredients, and the composition of other supplements the correct percentage (%) by weight, does not retain any major fragrance of disinfectant bacteria, antiviral, and neutralizing SARS-CoV-2 virus to which the present invention is concerned; (d) Homogeneous solution mixes act as a reactant, allowing the addition of ingredients to contribute their chemical and physical properties to create a new preparation; (e) Homogeneous solution chemically bonds with the plant extracts/essential oils, *betel* leaf extracts/essential oils, 4-allylpyrocatechol (APC) ingredients, and the composition of other supplements including but not limited to ionization reactions, covalent reactions, reducing reactions, replacement reactions, and rearrangement reactions to form a new chemical composition.

Still with FIG. 1, continue to the second stage of 200B, admixing ingredient C and the homogeneous solution, wherein the ingredient C is a gelatin ingredient of a predetermined percentage (%) by weight, to create a temporary solution. It should be noted that the term "admixed/mixed/admixing/mixing" as used in the present invention is understood to mean adding, or reacting, or dissolving homogeneously, or evenly, components in the same solution/mixture.

Finally, the third stage at 200C, mixing the temporary solution with 4-allylpyrocatechol (APC), plant extracts/essential oils, and *betel* leaf extracts/essential oils of a predetermined percentage (%) by weight, to create a foundation solution is intended to increase bactericidal, antiviral activity, and neutralizing activity of the SARS-CoV-2 virus. However, in an exemplary embodiment of the present invention, the ingredient 4-allylpyrocatechol (APC), the plant extract/essential oil component, and the *betel* leaf extract/essential ingredient is added in a particular order. Namely, the 4-allylpyrocatechol (APC) ingredient admixed first, then the plant extract/essential oil, and finally the *betel* leaf extract/essential oil. It should be noted that when 4-allylpyrocatechol (APC) ingredient, the plant extracts/essential oils, and *betel* leaf extracts/essential oils are not admixed in the specific order described, the final product will not have bactericidal, antiviral, and neutralizing of virus SARS-CoV-2.

Figure 2:
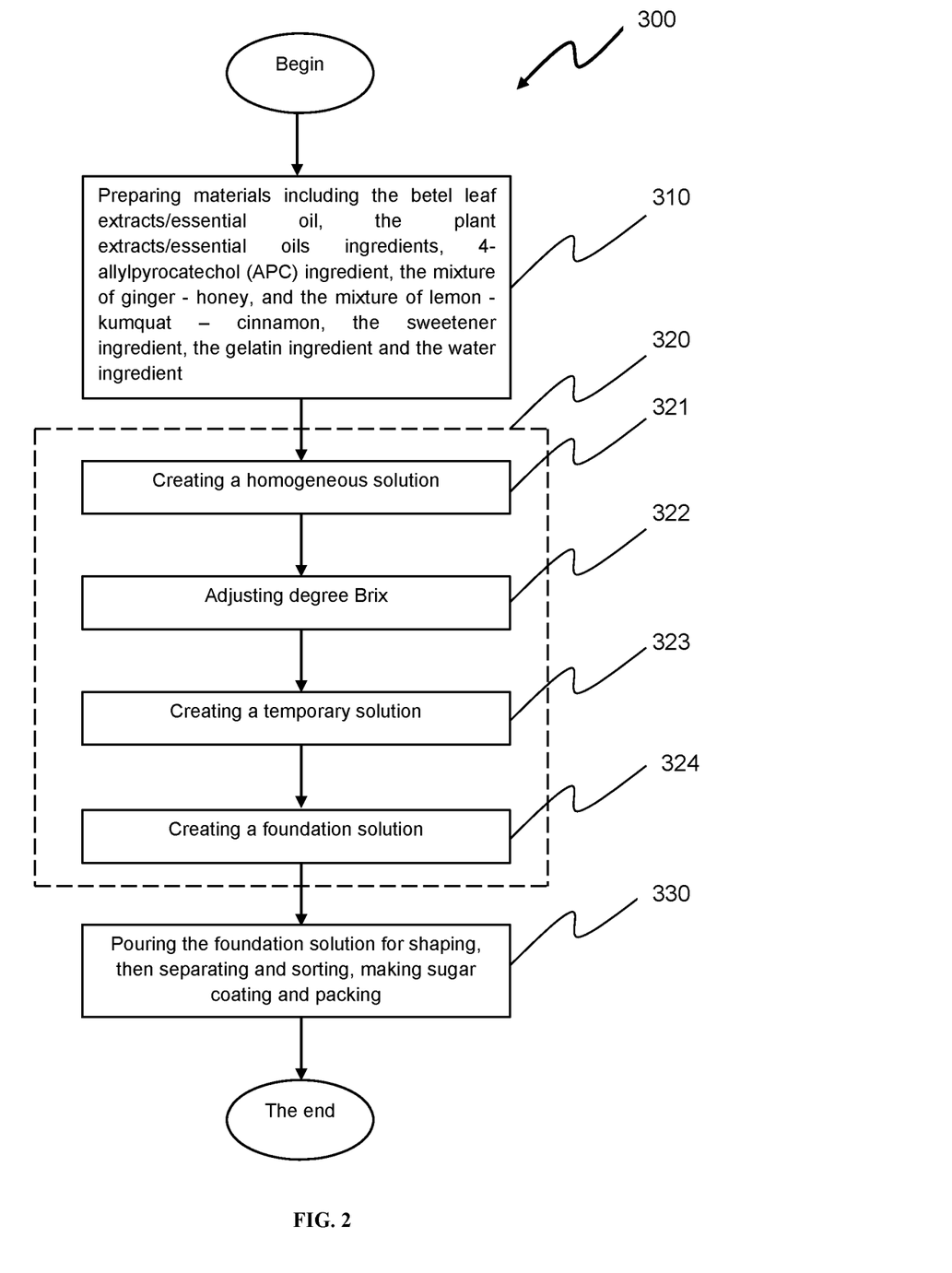
FIG. 2 is a flowchart illustrating a flowchart of a general method of manufacturing the composition having oral cavity delivery agent confectionery/candy based on the above principle in accordance with an exemplary embodiment of the present invention.

Now referring to FIG. 2, the method of manufacturing the composition having oral cavity delivery agent confectionery/candy 300 ("method 300") based on the above principle in accordance with an exemplary embodiment of the present invention. In particular, method 300 includes the following steps:

At step 310, preparing materials including the *betel* leaf extracts/essential oil, the plant extracts/essential oils ingredients, 4-allylpyrocatechol (APC) ingredient, the mixture of ginger-honey, and the mixture of lemon-kumquat-cinnamon; all the ingredients are carefully prepared and stored in separate instruments.

As the plant extract in the present invention, an "extracts/essential" extracted as an aromatic substance contained in the above-mentioned plants is preferable. The essential oil in a narrow sense obtained by steam distillation from the above plants or dried materials thereof is preferably used as the "extracts/essential oil" in the present invention, but is not limited thereto. For example, oils extracted from the plants by using other methods such as extraction or expression are also included in the "extracts/essential oil" of the present invention as long as they contain essential oil components (such as aromatic substances). As other methods for extracting essential oils from plants, for example, solvent extraction (such as alcohol extraction, organic solvent extraction), oil and fat adsorption extraction (hot enfleurage or cold enfleurage), and supercritical fluid extraction are known. When the steam distillation cannot be applied because of a low essential oil content in the plant and the like, the solvent extraction is often used. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts/essential oil" in the present invention may be those in which the oil obtained by the above method is further purified and concentrated by using various purification procedures such as hydrophobic or adsorptive chromatography using a support such as porous beads, silica gel, or alumina.

According to the embodiment of the present invention, the mixture of ginger-honey is obtained by mixing the ginger ingredient and the honey solution combined with stirring 30-40 rpm in five minutes, then fermentation for 30-180 minutes at a temperature of 25° C.-300° C.

According to the embodiment of the present invention, the mixture of lemon-kumquat-cinnamon is obtained by mixing the lemon pure juice with the cinnamon ingredient combined with stirring 30-40 rpm in five minutes, then adding the kumquat pure juice combined with stirring 30-40 rpm in five minutes and soaking for 10-15 minute.

Still with FIG. 2, at step 320, mixing the ingredients prepared in step 310 including steps 321, 322, 323, and 324. Namely, at step 321, creating a homogeneous solution by mixing the water ingredient with the sweetener ingredient combined with stirring 25-50 rpm in 10-15 minutes at a temperature of 75° C.-85° C. Then, adding the mixture of ginger-honey, and the mixture of lemon-kumquat-cinnamon combined with stirring 25-50 rpm in 3-10 minutes.

At step 322, heating and stirring the homogenizer solution in step 321 with stirring 40-70 rpm for 5 minutes; determining whether degree Brix of the homogeneous solution is had reaches 75°Bx-85°Bx; if degree Brix of the homogeneous solution not reach 75°Bx-85°Bx, adding the sweetener ingredient, and repeating said step 322 until said degree Brix of the homogeneous solution having reach 75°Bx-85°Bx.

At step 323, creating a temporary solution by mixing the gelatin ingredient with the homogeneous solution combined with stirring 30-50 rpm in 5 minutes.

At step 324, creating a foundation solution by mixing the 4-allylpyrocatechol (APC) ingredient, the plant extracts/essential oils ingredients, with the *betel* leaf extracts/essential oil, and the temporary solution combined with stirring 50-80 rpm in 1-2 minutes.

Finally, at step 330, pouring the foundation solution for shaping, then separating and sorting, making sugar coating and packing.

The composition of the present invention contains plant extracts, non-toxic, safe to use, and limits cross-infection from bacteria and viruses through the respiratory tract; 99.99% bactericidal efficiency, has antiviral ability in general, and contributes to the prevention of coronavirus in particular. Contributing to diversifying products, promoting the strengths of medicinal plants in general, and *piper betel* L. in particular. In addition, take advantage of natural herbs that are popular and available in Vietnam local at a low cost. The effect of inhibiting the proliferation of the SARS-CoV-2 virus, thus, providing prevention and support in the treatment of acute respiratory infections caused by the SARS-CoV-2 virus and at the same time helping to improve physical health and psychological stability for patients.

TABLE 1

Test results for cell toxicity Vero E6 of a betel leaf extracts/essential oil with different dilutions/serial dilutions

| Dilutions | Results |
|---|---|
| Control Cells | No cell damage |
| $10^{-1}$ | No cell damage |
| $10^{-2}$ | No cell damage |
| $10^{-3}$ | No cell damage |
| $10^{-4}$ | No cell damage |
| $10^{-5}$ | No cell damage |
| Result | No cell damage |

TABLE 2

Results of neutralization of virus Sars-CoV-2 when a betel leaf extracts/essential oil is exposed/exposed to the virus Sars-CoV-2 for thirty minutes with different dilutions/serial dilutions

| Dilutions | Control sample results | Test sample results |
|---|---|---|
| $10^{-1}$ | ++++ | ++++ |
| $10^{-2}$ | ++++ | 0000 |
| $10^{-3}$ | ++++ | 0000 |
| $10^{-4}$ | ++++ | 0000 |
| $10^{-5}$ | +++0 | 0000 |
| $10^{-6}$ | +000 | 0000 |
| $10^{-7}$ | 0000 | 0000 |
| $10^{-8}$ | 0000 | 0000 |
| $TCID_{50}/0.1$ mL | $10^{5,5}$ | $10^{1,5}$ |
| | Conclusion | Standard: BS EN 14476: 2013 + A2:2019 |
| Test sample | 4 $\log_{10}$ | ≥4 $\log_{10}$ | in which: (+) means having the presence of a virus;
(0) means don't have the presence of a virus;
Control sample: virus Sars-CoV-2;
Test sample: The *betel* leaf extracts/essential oil is exposed/exposed to the virus Sars-CoV-2 for 30 minutes.

TABLE 3

Some plants having active are used as plant extracts/essential oils ingredients in the embodiment of the present invention

| No. | Plants | Species | Collection region | Active Compounds | Mechanism of Action |
|---|---|---|---|---|---|
| 1 | Chinese liquorice | *Glycyrrhiza uralensis* Fisch | Northern Vietnam | Echinatin | Against HIV, RSV, Herpes viruses, Coronavirus (SARS-CoV) |
| 2 | Liquorice | *Glycyrrhiza glabra* L | | Glycyrrhizin, Glycyrrhetic acid, Glabridin, Liquiritin | Against Corona virus, type A influenza virus, Japanese encephalitis, Herpes simplex, Vesicular stomatitis |

TABLE 3-continued

Some plants having active are used as plant extracts/essential oils ingredients in the embodiment of the present invention

| No. | Plants | Species | Collection region | Active Compounds | Mechanism of Action |
|---|---|---|---|---|---|
| | | | | | virus, Newcastle disease virus (NDV) |
| 3 | Tea | Camellia sinensis | Vietnam | Polyphenols (Sanguiin, Theaflavin gallate, Theaflavin digallate, Kaempferol, Punicalagin and Protocatechuic acid) | Inhibiting the activity of SARS-CoV-2 main protease (Mpro) |
| 4 | Holy basil | Ocimum sanctum | Vietnam | Apigenin, Linalool and Ursolic acid | Antiviral activities |
| 5 | Turmeric | Curcuma domestica | Vietnam | Curcumin | Restrained viral protease enzyme by inhibiting amino acid synthesis. |
| 6 | Clove | Syzygium aromaticum | Vietnam | Eugenol, Thymol, Eugenil acetat, Gallic acid, Beta cariophyllene | Antiviral by inhibiting viral DNA polymerase enzyme, then preventing DNA synthesis |
| 7 | Aloe vera | Aloe vera | Vietnam | Aloenin, Aloesin | Potential inhibitors of COVID-19 proteases. |
| 8 | Globe artichoke | Cynara Scolymus L | Vietnam | Cynaropicrin | Inhibit viral cell-entry (Hepatitis C virus) |
| 9 | Roselle | Hibiscus sabdariffa | Vietnam | Hibiscus acid, Citric acid | Inhibited viral replication and viral antigens and genes expression |
| 10 | Bitter melon | Momordica charan | Vietnam | Momordicine, Charantin | Inhibit various stages of viral life cycle |
| 11 | Basil | Ocimum sanctum L | Vietnam | Eugenol, linolenic acid | Inhibit protease enzym |
| 12 | Pomegranate | Punica granatum L. | Vietnam | Polyphenols, Ursolic acid | Inhibits viral replication (Influenza virus) |
| 13 | Chamber bitter | Phyllanthus urinaria L | Vietnam | 1,3,4,6-Tetra-O-galloyl-d-glucose (1346TOGDG), Excoecarianin | Antiviral activities |
| 14 | Lemon balm | Melissa officinalis | Vietnam | Monoterpenaldehydes citral | Antiviral activities |
| 15 | Mint | Mentha haplocalyx Brig. | Northern Vietnam | Spicatoside A, Spicatoside B, Menthalactone, Maniladiol | Resistance to SARS-CoV |
| 16 | Horseradish tree | Moringa oleifera Lam. | Vietnam | O-ethyl-4- (α-L-rhamnosyloxy); benzyl carbamate; 4 (α Lrhamnosyloxy)-benzyl isothiocyanate; Niazimicin; Niazirin; P-sitosterol; Glycerol-1-(9-octadecanoate); 3 -0- 6 -O-oleoyl- β-Dglucopyranosyl b-sitosterol; β | Resistance to EBV-EA (Epstein- Barr virusearly antigen) |

TABLE 3-continued

Some plants having active are used as plant extracts/essential oils ingredients in the embodiment of the present invention

| No. | Plants | Species | Collection region | Active Compounds | Mechanism of Action |
|---|---|---|---|---|---|
| 17 | White mulberry | *Morus alba* L | Vietnam | sitosterol- 3-X-O -β-Dglucopyranoside Kuwanon S, Mulberroside C, Cyclomorusin, Eudraflavone B Hydroperoxide, Oxydihydromorusin, Leachianone G and α-acetyl-amyrin | Resistance to Herpes simplex type 1 virus (HSV-1), FMD virus, Foot-and-mouth disease virus |
| 18 | Ginger | *Zingiber officinale* Rosc | Vietnam | Arcurcumene, β-sesquiphellandrene, α zingiberene and β-bisabolene, Flavan and 4, 6-dichloroflavan | Resistance to Rhinovirus IB |
| 19 | Cinnamon | *Cinnamomum zeylanicum* Blume | Vietnam | cinnamaldehyde, caryophyllene, α-caryophyllene | Angiotensin converting enzyme (ACE) inhibitors activity of Coronavirus |
| 20 | Broad-leaved plantain | *Plantago major* L. | Vietnam | Caffeic acid, chlorogenic acid | Antiviral activities |
| 21 | Areca nut palm | *Areca catechu* L. | Vietnam | Arecoline, Arecaidine, Guvacine, Guvacoline, Arecolidine, Homoarecoline | Resistance to SARS-CoV |
| 22 | Apricot | *Prunus armeniaca* L. | Northern Vietnam | Amygdalin, Neoamygdalin and Amygdalin Amide | Resistance to SARS-CoV |
| 23 | Lanxangia tsaoko | *Lanxangia tsaoko* | Northern Vietnam | Cineole | Resistance to SARS-CoV |
| 24 | Avocado | *Persea americana* | Vietnam | Tannins, Saponins, Flavonoids, Alkaloids, Cyanogenic glycosides | Antimicrobial |
| 25 | Lemongrass | *Cymbopogon citratus* | Vietnam | Citral | Antimicrobial |
| 26 | Lemongrass | *Cymbopogon winterianus* J. | Vietnam | Geraniol; Citronella | Antimicrobial |
| 27 | Lemongrass | *Cymbopogon flexuosus* Stapf. | Vietnam | Citral | Antimicrobial |
| 28 | Siamese ginger | *Alpinia officinarum* | Vietnam | Curcumin | SARS-CoV-2 papain-like protease (PLpro) inhibitors |
| 29 | Red amaranth | *Amaranthus tricolor* | Vietnam | Amaranthin | Inhibited SARS-CoV-2 3CL proactivity and virus replication. |
| 30 | Tufuling | *Smilax glabra* Roxb | Vietnam | Mannose-binding lectin, Narcissus tazetta lectin | Antiviral activities |

TABLE 4

Some Citrus/Citrus fruits are used in the embodiment of the present invention

| No. | Citrus/Citrus fruits | Species | Collection region | Active Compounds | Mechanism of Action |
|---|---|---|---|---|---|
| 1 | Orange | *Citrus sinensis* | Vietnam | Limonene, β-myrcene, α-pinene, γ-terpinene, linalool, β-pinene | Antibacterial Anti-influenza virus Inhibit coronavirus replication |
| 2 | Lemon Lime | *Citrus lemon* *Citrus aurantifoli* | Vietnam | Limonene, β-myrcene, γ-terpinene, geranial, sabinene, neral, β-pinene, α-pinene | Antibacterial Inhibit virus replication |
| 3 | Kumquat | *Citrus japonica* '*Japonica*' | Vietnam | C-glycosylated flavones, C-glycosylated flavones, O-glycosylated flavones, O-glycosylated flavones, flavonols, phenolic acids, chalcones | Antioxidant and Antimicrobial |
| 4 | Pomelo grapefruits | *Citrus maxima/ Citrus grandis Citrus paradisi* | Vietnam | Limonene, β-myrcene, α-pinene, 7-geranoyloxycoumarin, β- pinene, γ-terpinene, linaloo | Antibacterial |
| 5 | Mandarin/ Clementina/ Tangerine | *Citrus reticulate* L | Vietnam | Limonene, γ- terpene, β- myrcene, α-pinene, decanal, β-pinene | Antibacterial |

TABLE 5

Mixed components of the composition 100 having oral cavity delivery agent confectionery/candy in the embodiment of the present invention

| No. | Name of | Percentage (%) | Preferably percentage (%) |
|---|---|---|---|
| 1 | Ginger powder | 0.5-1.5 | 1 |
| 2 | Honey solution | 2.5-7.5 | 5 |
| 3 | Lemon pure juice | 2-5 | 2.5 |
| 4 | Kumquat pure juice | 2-5 | 2.5 |
| 5 | Cinnamon | 0.4-1 | 0.5 |
| 6 | Plant extracts/essential oils + | 1 | 1 |
|  | Lemongrass + | 0.5 | 0.5 |
|  | Mint | 0.5 | 0.5 |
| 7 | Betel leaf extracts/essential oil | 0.5 | 0.5 |
| 8 | Gelatin | 3-6 | 4-5 |
| 9 | Sweetener | 50-70 | 60 |
| 10 | APC | 0.12-0.2 | 0.15-0.18 |
| 11 | Water | rest | rest |

According to the embodiment of the present invention, the production method produces 100 kilograms of the composition 100 having oral cavity delivery agent is confectionery/candy, including three examples listed in Table 6 below.

TABLE 6

Mixed components of the composition 100 having oral cavity delivery agent confectionery/candy in three examples according to the embodiment of the present invention

| | | Weight (kg) | | |
|---|---|---|---|---|
| No. | Name of | Example 1 | Example 2 | Example 3 |
| 1 | Ginger powder | 1 | 1 | 1 |
| 2 | Honey solution | 5 | 5 | 5 |
| 3 | Lemon pure juice | 2.5 | 2.5 | 2.5 |
| 4 | Kumquat pure juice | 2.5 | 2.5 | 2.5 |
| 5 | Cinnamon | 0.5 | 0.5 | 0.5 |
| 6 | Lemongrass extracts/essential oil | 0.5 | 0 | 0.5 |
| 7 | Mint extracts/essential oil | 0.5 | 0.5 | 0 |
| 8 | Betel leaf extracts/essential oil | 0.5 | 0.5 | 0.5 |
| 9 | Gelatin | 5 | 5 | 5 |
| 10 | Sweetener | 6 | 6 | 6 |
| 11 | APC | 0.16 | 0.16 | 0.16 |
| 12 | Water | rest | rest | rest |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. An oral composition containing extracts of a *betel* leaf comprising:
   a) an oral cavity delivery agent is confectionery/candy;
   b) an antimicrobial active agent and neutralizing for virus SARS-CoV-2 including a *betel* leaf extracts/essential oil combined with a plant extracts/essential oils ingredients, 4-allylpyrocatechol (APC) active compound, a mixture of ginger-honey, and a mixture of lemon-kumquat-cinnamon;
   c) other ingredients including a sweetener ingredient, a gelatin ingredient and water;
   wherein said plant extracts/essential oils ingredients selected from the one or more of the following chinese liquorice (*Glycyrrhiza uralensis* Fisch.), liquorice (*Glycyrrhiza Glabra* L.), tea (*Camellia sinensis*), holy basil (*Ocimum sanctum*), globe artichoke (*Cynara Scolymus* L.), roselle (*Hibiscus sabdariffa*), bitter melon (*Momordica charan*), basil (*Ocimum sanctum* L.), pomegranate (*Punica granatum* L.), chamber bitter (*Phyllanthus urinara* L.), lemon balm (*Melissa officinalis*), mint (*Mentha haplocalyx* Briq.), horseradish tree (*Moringa oleifera* Lam.), white mulberry (*Morus alba* L.), broad-leaved plantain (*Plantago major* L.), areca nut palm (*Areca catechu* L.), apricot (*Prunus armeniaca* L.), lanxangia tsaoko (*Lanxangia tsaoko*), avocado (*Persea americana*), lemongrass (*Cymbopogon citratus, Cymbopogon winteranus J., Cymbopogon flexuosus* Stapf.), siamese ginger (*Alpinia officinarum*), red amaranth (*Amaranthus tricolor*), and tufuling (*Smilax glabra* Roxb);
   wherein said antimicrobial active agent and neutralizing for virus SARS-CoV-2 including the *betel* leaf extracts/ essential oil combined with a lemongrass extracts/ essential oil ingredient, a mint extracts/essential oil ingredient, 4-allylpyrocatechol (APC) active compound, the mixture of ginger-honey, and the mixture of lemon-kumquat-cinnamon;
   the gelatin ingredients extracted from plants or animals; and treated by soaking with water in the respective ratio of 1:2;
   the *betel* leaf extract/essential oil and 4-allylpyrocatechol (APC) active compound extracted from fresh old *betel* leaves crushed/chopped/or not chopped, immersed are soaked in solvent, or brine solution; wherein a total time from harvesting and preserving fresh old *betel* leaves from the *betel* nut tree must be less than 55 minutes;
   the mixture of ginger-honey is obtained by mixing a ratio of a ginger ingredient and a honey solution having 1:5, combined with stirring 30-40 rpm in five minutes, then fermentation for 30-180 minutes at a temperature of 25° C.-30° C.; wherein the ginger ingredient is a ginger powder;
   the mixture of lemon-kumquat-cinnamon is obtained by mixing a lemon with a cinnamon ingredient combined with stirring 30-40 rpm in five minutes, then adding a kumquat combined with stirring 30-40 rpm in five minutes and soaking for 10-15 minute; wherein a ratio of mixing a lemon juice:a kumquat juice:a cinnamon ingredient having 5:5:1;
   wherein the cinnamon ingredient is a cinnamon powder.

2. The composition of claim 1, wherein a ratio of the antimicrobial active agent and neutralizing for virus SARS-CoV-2 and other ingredients having 1: (5.5-9.5).

3. The composition of claim 2, wherein a ratio of the antimicrobial active agent and neutralizing for virus SARS-CoV-2 and other ingredients having 1:(6-7).

4. The composition of claim 1, wherein a ratio of the total of the *betel* leaf extracts/essential oil and the plant extracts/ essential oils ingredients with the mixture of ginger-honey, and the mixture of lemon-kumquat-cinnamon having (1-3): 12:11.

5. The composition of claim 4, wherein the ratio of the total of the *betel* leaf extracts/essential oil and the plant extracts/essential oils ingredients with the mixture of ginger-honey, and the mixture of lemon-kumquat-cinnamon having 1:12:11.

6. The composition of claim 4, wherein the ratio of the total of the *betel* leaf extracts/essential oil and the plant extracts/essential oils ingredients with the mixture of ginger-honey, and the mixture of lemon-kumquat-cinnamon having 2:12:11.

7. The composition of claim 4, wherein the ratio of the total of the *betel* leaf extracts/essential oil and the plant extracts/essential oils ingredients with the mixture of ginger-honey, and the mixture of lemon-kumquat-cinnamon having 3:12:11.

8. The composition of claim 1, wherein a ratio of the *betel* leaf extracts/essential oil and the plant extracts/essential oils ingredients having 1:(1-3).

9. The composition of claim 8, wherein the ratio of the *betel* leaf extracts/essential oil and the plant extracts/essential oils ingredients having 1:2.

10. The composition of claim 8, wherein the ratio of the *betel* leaf extracts/essential oil and the plant extracts/essential oils ingredients having 1:1.

11. The composition of claim 1, wherein a ratio of the *betel* leaf extracts/essential oil and 4-allylpyrocatechol (APC) active compound having 3:1.

12. The composition of claim 11, wherein the ratio of the *betel* leaf extracts/essential oil and 4-allylpyrocatechol (APC) active compound is three parts of the *betel* leaf extracts/essential oil obtained from fresh, old *betel* leaves distilled with the saturated brine solution corresponds to one part of 4-allylpyrocatechol (APC) active compound.

13. The composition of claim 11, wherein the ratio of the *betel* leaf extracts/essential oil and 4-allylpyrocatechol (APC) active compound is three parts of the *betel* leaf extracts/essential oil obtained from fresh, old *betel* leaves distilled with the solvent corresponds to one part of 4-allylpyrocatechol (APC) active compound.

14. The composition of claim 1, a ratio of the antimicrobial active agent and neutralizing for virus SARS-CoV-2 with a total of the sweetener ingredient and the water, and the gelatin ingredient having (2-3):(15-20):1.

15. The composition of claim 14, the ratio of the antimicrobial active agent and neutralizing for virus SARS-CoV-2 with a total of the sweetener ingredient and the water, and the gelatin ingredient having 2.5:16.5:1.

16. The composition of claim 14, the ratio of the antimicrobial active agent and neutralizing for virus SARS-CoV-2 with a total of the sweetener ingredient and the water, and the gelatin ingredient having 2.6:16.4:1.

17. The composition of claim 1, wherein the composition having oral cavity delivery agent confectionery/candy is obtained by a method comprising the steps of:
(i) preparing materials including
the antimicrobial active agent and neutralizing for virus SARS-CoV-2 including the *betel* leaf extracts/essential oil combined with the lemongrass extracts/essential oil ingredient, the mint extracts/essential oil ingredient, 4-allylpyrocatechol (APC) active compound, the mixture of ginger-honey, and the mixture of lemon-kumquat-cinnamon;
other ingredients including the sweetener ingredient, the gelatin ingredient, and the water;
the mixture of ginger-honey is obtained by mixing the ginger ingredient and the honey solution combined with stirring 30-40 rpm in five minutes, then fermentation for 30-180 minutes at a temperature of 25° C.-30° C.; wherein the ginger ingredient is a ginger powder;
the mixture of lemon-kumquat-cinnamon is obtained by mixing the lemon juice with the cinnamon ingredient combined with stirring 30-40 rpm in five minutes, then adding the kumquat juice combined with stirring 30-40 rpm in five minutes and soaking for 10-15 minute; wherein a ratio of mixing a lemon juice:a kumquat juice:a cinnamon ingredient having 5:5:1;
wherein the cinnamon ingredient is a cinnamon powder;
the gelatin ingredients extracted from plants or animals; and treated by soaking with water in the respective ratio of 1:2;
the *betel* leaf extract/essential oil and 4-allylpyrocatechol (APC) active compound extracted from fresh old *betel* leaves crushed/chopped/or not chopped, immersed are soaked in solvent, brine solution; wherein a total time from harvesting and preserving fresh old *betel* leaves from the *betel* nut tree is 30-45 minutes;
(ii) mixing the material in step (i) in four stages:
stage 1: mixing the water with the sweetener ingredient combined with stirring 25-50 rpm in 10-15 minutes at a temperature of 75° C.-85° C.;
then, adding the mixture of ginger-honey, and the mixture of lemon-kumquat-cinnamon combined with stirring 25-50 rpm in 3-10 minutes creating a homogeneous solution;
stage 2: stirring the homogeneous solution with 40-70 rpm in 5 minutes;
determining whether degree Brix of the homogeneous solution is had reaches 75°Bx-85°Bx;
if degree Brix of the homogeneous solution not reach 75°Bx-85°Bx, adding the sweetener ingredient, and repeating said steps of stage 2 until said degree Brix of the homogeneous solution having reach 75°Bx-85°Bx;
stage 3: creating a temporary solution by mixing the gelatin ingredient with the homogeneous solution combined with stirring 30-50 rpm in 5 minutes;
stage 4: creating a foundation solution by mixing the 4-allylpyrocatechol (APC) active compound, the lemongrass extracts/essential oil ingredient, the mint extracts/essential oil ingredient, with the *betel* leaf extracts/essential oil, and the temporary solution combined with stirring 50-80 rpm in 1-2 minutes;
(iii) pouring the foundation solution for shaping, then separating and sorting, making sugar coating and packing.

18. The composition of claim 17, wherein the composition comprising:
(a) the ginger powder having 0.5%-1.5% by weight;
(b) the honey solution having 2.5%-7.5% by weight;
(c) the lemon juice having 2%-5% by weight;
(d) the kumquat juice having 2%-5% by weight;
(e) the cinnamon ingredient having 0.4%-1% by weight;
(f) the lemongrass extracts/essential oil ingredient having 0.5% by weight;
(g) the mint extracts/essential oil ingredient having 0.5% by weight;
(h) the *betel* leaf extracts/essential oil having 0.5% by weight;
(i) the gelatin ingredient having 3%-6% by weight;
(j) the sweetener ingredient having 50%-70% by weight;
(k) the 4-allylpyrocatechol (APC) compound having 0.12%-0.2% by weight; and
(l) the remainder is the water.

19. The composition of claim 18, wherein the composition comprising:
(a) the ginger powder having 1% by weight;
(b) the honey solution having 5% by weight;
(c) the lemon juice having 2.5% by weight;
(d) the kumquat juice having 2.5% by weight;
(e) the cinnamon ingredient having 0.5% by weight;
(f) the lemongrass extracts/essential oil ingredient having 0.5% by weight;
(g) the mint extracts/essential oil ingredient having 0.5% by weight;
(h) the *betel* leaf extracts/essential oil having 0.5% by weight;
(i) the gelatin ingredient having 4%-5% by weight;
(j) the sweetener ingredient having 60% by weight;

(k) the 4-allylpyrocatechol (APC) active compound having 0.15%-0.18% by weight; and
(l) the remainder is the water.

* * * * *